United States Patent
Alther

(12) 
(10) Patent No.: US 6,503,740 B1
(45) Date of Patent: Jan. 7, 2003

(54) ORGANICALLY MODIFIED MINERAL MATERIALS CONTAINING ENGRAFTED BACTERIA FOR CHEMICAL CONTAMINANT DECOMPOSITION

(75) Inventor: George Alther, Ferndale, MI (US)

(73) Assignee: Biomin, Inc., Ferndale, MI (US)

( * ) Notice: Subject to any disclaimer, the term of this patent is extended or adjusted under 35 U.S.C. 154(b) by 0 days.

(21) Appl. No.: 09/617,571

(22) Filed: Jul. 17, 2000

(51) Int. Cl.[7] .................. C12N 11/14; C12N 11/02; B09B 3/00; C02F 3/00
(52) U.S. Cl. ................ 435/176; 210/601; 210/610; 210/615; 210/616; 435/177; 435/262.5
(58) Field of Search ................ 435/176, 177; 210/601, 610, 615, 616

(56) References Cited

U.S. PATENT DOCUMENTS

| | | | |
|---|---|---|---|
| 3,935,067 A | 1/1976 | Thayer | 435/397 |
| 4,177,144 A | 12/1979 | Hickey et al. | 210/86 |
| 4,402,881 A | * 9/1983 | Alther | 260/448 |
| 4,620,929 A | 11/1986 | Hofmann | 210/610 |
| 6,080,319 A | * 6/2000 | Alther | 210/679 |
| 6,093,241 A | * 7/2000 | Alther | 106/719 |

OTHER PUBLICATIONS

"Understanding Anaerobic Treatment," *Pollution Engineering*, pp. 36–38 (Feb. 2000).

* cited by examiner

*Primary Examiner*—David M. Naff
(74) *Attorney, Agent, or Firm*—Dierker & Glassmeyer, P.C.

(57) ABSTRACT

A treatment media is provided capable of acting upon at least one chemical contaminant in an aqueous composition and assisting in the decomposition thereof. The treatment media is a biologically activated organically modified material which includes a mineral based substrate, selected from the group consisting of clays, clay analogs, synthetic resins, zeolites and mixtures thereof. The mineral based substrate is treated with an organic modification compound selected from the group consisting of quaternary amines, pyridinium compounds, phosphonium amines, and mixtures thereof. At least one strain of bacteria is engrafted to the mineral-based substrate, the bacteria being capable of facilitating decomposition of the chemical contaminant. Quaternary amines used provide enhancement of bacterial colonies and do not adversely effect bacterial activity when employed as the organic modification compound to treat the mineral based substrate. Preferred quaternary amines include ditallow dimethyl ammonium chloride, hexadecyl ammonium chloride, octadecyl ammonium chloride, di-methyl di-hydrogenated tallow ammonium chloride, and dicocodimethyl ammonium chloride.

9 Claims, No Drawings

ORGANICALLY MODIFIED MINERAL MATERIALS CONTAINING ENGRAFTED BACTERIA FOR CHEMICAL CONTAMINANT DECOMPOSITION

BACKGROUND OF THE INVENTION

The present invention pertains to organically modified minerals which are biologically activated. More particularly, the present invention pertains to organically modified mineral materials on which select biologically active organisms are grafted. The present invention also pertains to methods for treating contaminated aqueous material using biologically activated organically modified minerals.

It has been ascertained that many types of bacteria useful in areas such as water purification systems exhibit enhanced growth and activity if permitted to grow on solid substrates. Such substrate—attached systems such as trickling filters and the like require relatively small amounts of maintenance and external care or input to function well.

In contrast, water treatment systems which employ activated sludge methodology or include large fermentation tanks require vast inputs of energy both to maintain the treatment organisms in suspension and to ensure that adequate oxygen is supplied to meet the oxygen demands of the system.

Various methods have been proposed for providing water treatment processes which employ bacteria fixed on solid substrate(s) in order to enhance existing treatment processes and render them more energy and labor efficient. Various substrates have been proposed for this purpose, such as sand or rock. Additionally, U.S. Pat. No. 4,620,929 to Hofmann and U.S. Pat. No. 3,935,067 to Thayer teach the use of expanded clay or plastic materials in combination with bentonite which advantageously exhibits moisture retention characteristics.

Other types of anaerobic filtration systems employ materials such as baked clay, sepiolite, or other clay materials such as vermiculite, attapulgite and the like. These materials have been found advantageous to bacteria fixation. Without being bound to any theory, it is believed that this is due to the presence of trace elements such as copper, zinc and magnesium. These trace elements are electrostatically fixed to the surface of the clay and can serve as nutrients for the bacteria.

Various methods have been proposed for achieving bacteria fixation on the surface of various solid substrates. U.S. Pat. No. 4,177,144 to Hickey et al. teaches pre-inoculation of granulated activated carbon with cellular material. The activated carbon adsorbs organic contaminants in a waste water source. The adsorbed contaminants are, in turn, digested by the bacteria.

Adsorption and bio-degradation are used in tandem to enhance biological treatment of the contaminated water. However, this waste water treatment method does have several drawbacks. As a result of the process, a thin film of biological and biologically-derived material can form around the carbon granules. The phenomenon can result in rapid diminution of adsorption capacity. Additionally, the bacteria will rest on the surface of the granules in a manner which blocks entrance to pores on the surface of the activated carbon preventing adsorption of contaminants in the waste water. Finally, materials such as activated carbon do not supply nutrients which encourage or promote bacterial growth or reproduction.

While cellular material such as bacteria will graft onto clay minerals and other materials, engraftment is enhanced when the material of choice possesses a surface charge such as is the case with both clays and zeolites. In such instances, the adsorption capacity of these minerals for bacteria is the ion exchange capacity.

It has also been found that organically modified materials such as organically modified bentonite or zeolite is efficacious in wastewater treatment processes. When a charged material such as bentonite or zeolite is organically modified, it still retains a good portion of its surface area to which bacteria can attach.

Effective biologically activated organically modified minerals have not been successfully produced. Without being bound to any theory, it is believed that this is due to the toxicity of organic modification agents such as quaternary amines to microbial material such as bacteria.

Thus, it would be desirable and is an object of the present invention to provide an organically modified mineral material which could be employed as a substrate for biologically active cellular material such as bacteria. It is a further object of the present invention to provide an organically modified mineral material which could provide nutrients for the bacteria engrafted thereon. Still further, it is an object of the present invention to provide a biologically activated organically modified material which could be used to reduce contaminants such as PCBs and dioxins from aqueous streams.

SUMMARY OF THE INVENTION

The present invention is directed to a treatment media capable of acting upon at least one chemical contaminant in an aqueous composition and assisting in the decomposition thereof. The treatment media is a biologically activated organically modified material which includes a mineral based substrate, selected from the group consisting of clay, clay analogs, synthetic resins, and mixtures thereof. The mineral based substrate is treated with an organic modification compound selected from the group consisting of quaternary amines, pyridinium compounds, phosphonium amines, and mixtures thereof. At least one strain of bacteria is engrafted to the mineral-based substrate, the bacteria being capable of facilitating decomposition of the chemical contaminant.

DETAILED DESCRIPTION OF THE PREFERRED EMBODIMENTS

This invention is predicated on the unexpected discovery that certain quaternary amines, when employed in context with substrate material are not significantly toxic toward select microbial treatment material such as bacteria. Without being bound to any theory, it is believed that this is due, at least in part, to the mediating nature of the substrate material such as, for example, bentonite or zeolite. It is also believed that these quaternary amines will exhibit an ability to fixate organic compounds in a manner which renders them amenable to bacterial digestion.

In the present invention, as broadly contemplated, micro-organism colonies are engrafted onto a suitable mineral-based substrate which has been organically modified by a suitable quaternary amine compound. The micro-organism colonies are generally made up of bacteria which exhibit ability to digest and/or break down organic pollutants present in an aqueous media to a simpler or more basic compound or compounds. Examples of compounds which can be processed in this manner include, but are not limited to polychlorinated biphenyls (PCB), dioxins, PNAH's, Phenolia, BTEX's, and the like. The microbial agents include various bacterial strains which would be known to those skilled in the art.

The suitable mineral-based substrate of the present invention is contemplated as one which is essentially water stable either in quiescent or agitated media. The material of choice will possess capacity for promoting bacterial engraftment. Preferably, the mineral-based substrate is a clay or clay analog or a synthetic resin suitable for use in water treatment. Suitable clay materials or clay analog materials include clays selected from the group consisting of bentonite, smectite, montmorillonite, paligorskite, attapulgite, sepiolite, saponite, kaolinite, halloysite, hectorite, beidellite and others. Other minerals include zeolites such as chabazite, clinoptilolite, and others. Yet other materials include stevensite, fire clay, ground shale, mud, and silt. Preferably, the clay material will be characterized as having a surface charge. Synthetic and natural materials having a surface charge are also contemplated as being suitable as the substrate of the present invention. It is to be understood that the materials contemplated as being suitable as the substrate, as well as equivalents thereof, may be used either alone, or a mixture of two or more of these materials may be used.

In the preferred embodiment, mineral-based substrate is selected from the group consisting of bentonites, zeolites and mixtures thereof.

In the present invention, the mineral-based substrate is organically modified by a suitable organic material from the group consisting of quaternary amines, phosphonium amines, pyridinium compounds, quaternary phosphonium chlorides, and mixtures thereof.

The manner in which organic modification occurs can be by any method known to those skilled in the art. Heretofore, it was believed that quaternary amines used to modify the surfaces of the substrates such as those discussed previously were biocidal and would de-activate bacterial material which came into contact with the amine material. The present invention is predicated on the unexpected discovery that specific classes of quaternary amines are non-biocidal to target bacteria. Indeed, it has been found that the quaternary amines employed in the present invention provide actual enhancement to the bacterial colonies inoculated on the surface of the clay or mineral material. Without being bound to any theory, it is believed that this is due to the ability of the quaternary amine material to provide alcoholic materials such as isopropyl alcohol in nutrient level concentration when the quaternary amine is employed to organically modify the substrate materials; particularly those specified in the foregoing discussion.

The quaternary amine employed in the process of the present invention is one which will be biologically supportive of inoculated bacteria, i.e., not adversely effect bacterial activity when the quaternary amine is employed to provide organically modified clays and mineral materials. The preferred quaternary amine can be generally characterized as an ammonium compound having 12 to 18 carbon atoms. The quaternary amines employed in the present invention are preferably selected from the group consisting of organically modified hydrogenated tallow ammonium chlorides, ditallow dimethyl ammonium chloride, hexadecyl and octadecyl ammonium chloride and derivatives thereof. Most preferably, the quaternary amine is selected from the group consisting of di-methyl di-hydrogenated tallow ammonium chloride, dicocodimethyl ammonium chloride, and mixtures thereof In the preferred embodiment, the quaternary amine of choice is employed at a ratio sufficient to provide organic modification without adversely affecting biological activity of the target microbes or their ability to graft on the available surface of the mineral material. The preferred range of quaternary amine to clay or mineral material is between about 10% to 100% amine to clay or mineral respectively, with a range between about 10% to 45% and about 10 g to 100 g being preferred; and ranges between about 36 g to 100 g, and 48 g to 100 g being most preferred. In a preferred embodiment, the mineral-based substrate and the organic surface modification compound are present in a ratio between about 10 parts to about 100 parts; and about 5 parts to about 150 parts, surface modification compound to mineral-based substrate respectively.

The term "target microbes" as used herein is defined as microbial material chosen for its specific bio-organic function in the desired application. One such non-limiting example of such bio-organic function is the degradation of petroleum derived hydrocarbons or other organic contaminants.

In the material of the present invention, bacteria graft onto the surface of the clay or mineral material without sufficient efficacy to permit formation of bioactive colonies. This engraftment is particularly enhanced when a charged material such as zeolite is employed. The basic adsorption capacity of these minerals for bacteria is the defined ion exchange capacity of the material. It has been found unexpectedly that organic modification of a charged material such as bentonite or zeolite with a quaternary amine such as those defined herein results in retention of a significant portion of the surface area of the material which becomes available for bacteria to attach to.

In order to prepare the biologically activated organically modified mineral material of the present invention, quantities of the mineral or clay substrate material or resin and quaternary amine material are blended in any suitable manner, in the proportions defined above, together with precultured bacteria in an aqueous medium. Blending may be accomplished by various devices such as a ribbon blender, extruder or the like. Particulars about the production of organically modified clays are generally known in the art and are as outlined in U.S. Pat. No. 4,402,881 issued to Alther, which is incorporated by reference herein in its entirety. After suitable mixing, the resulting material which typically has a slurry-like consistency is dried and either milled to a powder or granulated.

During the mixing process, nitrogen supplying nutrients such as standard fertilizer, urea and the like or carbon/ glucose supplying nutrients such as molasses and alcohol can be incorporated. If necessary, oxygenated material can also be incorporated by including slow-release sources of oxygen such as calcified seaweed or marl. Trace minerals can also be incorporated.

In general, the bacterial colony units are formed in water which is adsorbed by the clay material or mineral material or resin. The adsorbing material retains a portion of the water keeping the mix moist.

Having thus disclosed the present invention, the following examples are provided to further illustrate the present invention. These examples are provided for illustrative purposes and are not to be construed as limitative of the present invention.

EXAMPLE I

Biologically active organically modified clay material was prepared according to the present invention using the quaternary amine di-methyl di-hydrogenated tallow ammonium chloride on bentonite at ratios of 36 grams ammonium chloride compound per 100 grams bentonite and 45 grams ammonium chloride compound per 100 grams bentonite respectively. The toxicity of these respective materials to soil microbes including those capable of degrading petroleum hydrocarbons were determined by respirometric tests.

Respirometric tests indicated some decrease in metabolic $CO_2$ produced in the presence of the organically modified clay. In both cases, an 80% reduction in total microbial population was observed compared to a non-organically modified control over a two week period. In spite of this reduction of the total microbial populations, both organically modified clay materials sustained healthy populations of micro-organisms capable of degrading petroleum hydrocarbons.

The results are collected in Table I. At the end of 12 days, Clay 1, (containing 36 grams ammonium chloride compound per 100 grams bentonite) and Clay 2 (containing 45 grams ammonium chloride compound per 100 grams bentonite) showed decreased rates of respiration as compared to the control system. This suggests that the two organically modified clay materials possess limited toxicity towards the bacteria.

Both the total and specific microbial populations of the test systems showed a consistent decrease of the control system. Surprisingly, total kill was not evidenced. This indicated that clays which are organically modified with the ammonium chlorides of the type defined can be employed as active substrates for bio-remediation. The results of microbial enumeration are outlined in Table II.

TABLE I

Results of $CO_2$ Respirometric Tests

| Sample | T = 2 days | T = 6 days | T = 8 days | T = 11 days | T = 12 days |
|---|---|---|---|---|---|
| Control | 2,960 | 5,790 | 7,547 | 9,472 | 10,147 |
| CLAY 1 | 2,920 | 4,283 | 6,433 | 7,748 | 8,228 |
| CLAY 2 | 2,900 | 4,032 | 6,179 | 7,629 | 8,134 | all results are expressed in $\mu$mol CO2 released all results are an average of duplicates

EXAMPLE II

Suitable bio-remediation bacteria were preinoculated to bentonite clay during the manufacturing process outlined above. Pre-inoculation was accomplished by adding a pre-culture colony to the mixture during the blending process. The bacteria which were added were those known to digest the PCB, ALOCHLOR 1260. A conventional bio-reactor was set up which included the resulting powdered biologically active organically modified clay material. Water contaminated with ALOCHLOR 1260 having an initial PCB concentration of 222 ppm was passed through the reactor for a total contact time of 120 min. The water exiting the reactor was collected for a total of 800 gallons of water.

TABLE II

Results of Microbial Enumeration

| Sample | Total Population | Specific Population* |
|---|---|---|
| Control | $5.09 \times 10^{11}$ | $2.38 \times 10^{10}$ |
| CLAY 1 | $1.02 \times 10^{11}$ | $1.12 \times 10^{10}$ |
| CLAY 2 | $9.69 \times 10^{10}$ | $1.58 \times 10^{10}$ |

*measured as hexadecane degraders
all results are an average of duplicates

The ALOCHLOR 1260 content after treatment was 12 ppm.

After the project was completed, analysis of the biologically activated organically modified clay revealed no PCB; indicating that the PCB was digested or converted rather than retained in the organically modified media. In this instance, it was believed that the PCB was converted to sugar.

EXAMPLE III

Bacteria capable of digesting 1,4 dioxin were inoculated into an organically modified clay (bentonite modified by the ammonium chloride compound as outlined in Example I) during processing. A bio-reactor was set up in the manner outlined in Example II. Contaminated water was passed through the reactor at a rate of 0.5 gpm for a total contact time of 25 gph. The initial 1,4 dioxin content of the contaminated water was 1.4 ppm. The treated water was collected for a total of 2000 ml and analyzed for 1,4 dioxin. Total 1,4 dioxin content after treatment was 0.013 ppm.

Testing of the biologically active organically modified clay after the project was finished indicated no retained 1,4 dioxin. This supports the conclusion that the 1,4 dioxin was digested by bacterial action.

Without being bound to any theory,. it is believed that the biologically activated organically modified clay material of the present invention can trap or retain organic contaminants in the matrix fixing the contaminants for bacterial degradation. Organic modification is hypothesized as enhancing the ability of the matrix to trap or retain organic contaminants in a manner which enhances the ability of the bacteria to degrade the contaminant molecules. It is also theorized that the organic modification can actually imitate chemical breakdown in certain instances.

From the foregoing discussion and description, it can be appreciated that the biologically active organically modified clay material can be employed as an effective substitute for activated carbon in activated carbon vessels used in treatment of water contaminated by various petroleum based oils. Water contaminated with oil can be passed through the vessels in a manner which permits the organically modified clay material to fix the oil contaminant to the material in a manner which facilitates digestion by the associated bacteria. This renders the filter vessel essentially self-cleaning or self-regenerating.

While preferred embodiments, forms and arrangements of parts of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. A self-cleaning treatment media capable of acting upon at least one chemical contaminant in an aqueous composition assisting in the decomposition of that contaminant to at least one suitable lower molecular weight compound, the treatment media comprising:
   a mineral-based substrate present in granular form, the mineral-based substrate being a charged material selected from the group consisting of clays, clay analogs, synthetic resins and mixtures thereof;
   a compound capable of providing organic surface modification to a portion of the mineral-based substrate, the organic modification compound comprising quaternary amines, wherein the quaternary amines are selected from the group consisting of ditallow dimethyl ammonium chloride, hexadecyl ammonium chloride, octadecyl ammonium chloride, di-methyl di-hydrogenated tallow ammonium chloride, dicocodimethyl ammonium chloride, and mixtures thereof, and wherein the mineral-based substrate contains the organic modification compound; and
   at least one strain of microbial material engrafted on the surface of the mineral-based substrate containing the organic surface modification compound, the microbial material capable of facilitating decomposition of the at least one chemical contaminant in the aqueous composition;
   wherein the strain of microbial material has a biological activity, and wherein the organic surface modification compound is one which permits sufficient biological activity of the microbial material when the microbial material and the organic surface modification compound are both present on the mineral-based substrate.

2. The treatment media of claim 1 wherein the mineral-based substrate and the organic surface modification compound are present in a ratio between about 10 parts to about 100 parts and about 5 parts to about 150 parts, surface modification compound to mineral-based substrate respectively.

3. The treatment media of claim 1 wherein the strain of microbial material is present in sufficient quantity to provide at least partial decomposition of the at least one chemical contaminant.

4. A self-cleaning treatment media capable of acting upon at least one chemical contaminant in an aqueous composition and assisting in the decomposition thereof, the treatment media comprising:
   a charged mineral based substrate, selected from the group consisting of clay, clay analogs, synthetic resins, zeolites, and mixtures thereof;
   an organic modification compound comprising quaternary amines, wherein the quaternary amines are selected from the group consisting of ditallow dimethyl ammonium chloride, hexadecyl ammonium chloride, octadecyl ammonium chloride, di-methyl di-hydrogenated tallow ammonium chloride, dicocodimethyl ammonium chloride, and mixtures thereof, and wherein the mineral-based substrate contains the organic modification compound; and
   at least one strain of bacteria engrafted to the mineral-based substrate containing the organic modification compound, the bacteria capable of facilitating decomposition of the chemical contaminant.

5. The treatment media of claim 4 wherein the mineral-based substrate is a clay consisting of bentonite.

6. The treatment media of claim 4 wherein the organic modification compound is present in a ratio of between about 10% to about 100%, quaternary amine to mineral-based substrate, respectively.

7. The treatment media of claim 4 further comprising microbial nutrients present in sufficient quantity to sustain the engrafted bacteria, the nutrients selected from the group consisting of carbohydrate sources, nitrogen sources, mineral sources, alcohol sources, and mixtures thereof.

8. The treatment media of claim 4 further comprising a source of microbial oxygen, wherein the oxygen source is selected from the group consisting of sea marl, calcified non-marl seaweed, and mixtures thereof.

9. The treatment media of claim 4 wherein the mineral-based substrate is a clay or clay analog selected from the group consisting of bentonite, smectite, montmorillonite, paligorskite, attapulgite, sepiolite, saponite, kaolinite, halloysite, hectorite, beidellite, stevensite, fire clay, ground shale, mud, silt, and mixtures thereof.

* * * * *